United States Patent
Karandikar et al.

(10) Patent No.: US 9,481,879 B2
(45) Date of Patent: *Nov. 1, 2016

(54) PREPARATION OF STABILIZED CATALASE ENZYMES WITH A SURFACTANT

(71) Applicant: Avent, Inc., Alpharetta, GA (US)

(72) Inventors: Bhalchandra M. Karandikar, Beaverton, OR (US); Sunita J. Macwana, Tigard, OR (US); Zhongju Liu Zhao, Sherwood, OR (US)

(73) Assignee: Avent, Inc., Alpharetta, GA (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/186,154

(22) Filed: Feb. 21, 2014

(65) Prior Publication Data

US 2014/0170129 A1 Jun. 19, 2014

Related U.S. Application Data

(60) Provisional application No. 61/769,407, filed on Feb. 26, 2013.

(51) Int. Cl.
*C12N 9/08* (2006.01)
*C12N 9/68* (2006.01)
*C12N 9/96* (2006.01)

(52) U.S. Cl.
CPC ............ *C12N 9/96* (2013.01); *C12N 9/0065* (2013.01); *C12Y 111/01006* (2013.01)

(58) Field of Classification Search
USPC ........................................ 424/94.3; 435/188
IPC .............. A61K 38/00; C11D 10/04,1/38, 3/38, C11D 3/386; C12N 9/02, 9/08, 9/96
See application file for complete search history.

(56) References Cited

U.S. PATENT DOCUMENTS

| | | | |
|---|---|---|---|
| 2,689,203 A | 9/1954 | Lolli | |
| 3,006,815 A | 10/1961 | Scott | |
| 3,523,871 A * | 8/1970 | Yajima | C12N 9/96 435/188 |
| 3,933,588 A | 1/1976 | Dworschack et al. | |
| 3,954,974 A | 5/1976 | Herzog et al. | |
| 4,485,091 A | 11/1984 | Fitton | |
| 4,826,681 A | 5/1989 | Jacquet et al. | |
| 5,324,649 A * | 6/1994 | Arnold et al. | 435/187 |
| 5,380,764 A | 1/1995 | Herzog | |
| 5,792,090 A | 8/1998 | Ladin | |
| 6,045,813 A | 4/2000 | Ferguson et al. | |
| 6,485,950 B1 | 11/2002 | Kumar et al. | |
| 6,767,342 B1 | 7/2004 | Cantwell | |
| 7,160,553 B2 | 1/2007 | Gibbins et al. | |
| 8,148,316 B2 * | 4/2012 | DiCosimo et al. | 510/305 |
| 8,652,531 B2 | 2/2014 | Karandikar et al. | |
| 2001/0041188 A1 | 11/2001 | Gibbins et al. | |
| 2009/0074880 A1 | 3/2009 | Ladizinsky | |
| 2009/0202617 A1 | 8/2009 | Ward et al. | |
| 2009/0263539 A1 * | 10/2009 | Herdt | A23L 3/3508 426/8 |
| 2009/0317478 A1 | 12/2009 | Han et al. | |
| 2010/0311668 A1 * | 12/2010 | Farwick et al. | 514/18.8 |
| 2013/0048559 A1 * | 2/2013 | Bluchel | B01D 67/0093 210/632 |

FOREIGN PATENT DOCUMENTS

| | | | |
|---|---|---|---|
| CA | 859115 A | 12/1970 | |
| EP | 2 113 564 A1 | 11/2009 | |
| FR | 2 666 812 A1 | 3/1992 | |
| GB | 713720 A | 8/1954 | |
| GB | 918056 A | 2/1963 | |
| JP | 61-015685 A | 1/1986 | |
| KR | 10-0804096 B | 2/2008 | |
| WO | WO 9317721 A1 * | 9/1993 | ............... A61L 2/00 |
| WO | WO 2009102770 A1 * | 8/2009 | ............... C12N 9/98 |
| WO | WO 2013/017995 A2 | 2/2013 | |

OTHER PUBLICATIONS

Amo et al., 2002. Unique Presence of a Manganese Catalase in a Hyperthermophilic Archaeon, Pyrobaculum calidifontis VA1. Journal of Bacteriology, vol. 184, pp. 3305-3312.*
Ayorinde et al. 2000.Analysis of some commercial polysorbate formulations using matrix-assisted laser desorption/ionization time-of-flight mass spectrometry, Rapid Communications in Mass Spectrometry, vol. 14, pp. 2116-2124.*
Eberhardt et al. 2004. Immobilization of catalase from Aspergillus niger on inorganic and biopolymeric supports for H2O2 decomposition. Applied Catalysis B: Environmental, vol. 47, pp. 153-163.*
Mathur et al. 2005. Fenugreek and other lesser known legume galactomannan-polysaccharides: Scope for developments. Journal of Scientific & Industrial Research, vol. 64, pp. 475-481.*
Bergmeyer , H.(Ed.) 1965. Methods in Enzymatic Analysis, p. 893.*
Horozova et al. 1997. Adsorption, Catalytic and Electrochemical Activity of Catalase Immobilized on Carbon Materials. Z. Naturforsch. vol. 52c, pp. 639-644.*
Prakash et al. 2009. A Review on Direct Electrochemistry of Catalase for Electrochemical Sensors. Sensors , vol. 9, pp. 1821-1844.*
Di Risio, Sabina et al., "Adsorption and Inactivation Behavior of Horseradish Peroxidase on Cellulosic Fiber Surfaces," Journal of Colloid and Interface Science, vol. 338, 2009, pp. 410-419.
Application Bulletin, "Emulsifier-Free Moisturizing Lotion (O/W)—Prepare a Cold-Processed, Oil-in-Water Lotion Using Avicel® PC 591 Microcrystalline Cellulose," FMC BioPolymer, Mastering the Art of Innovative Thinking, Issue No. 1, Jan. 2004, 2 pages.

* cited by examiner

*Primary Examiner* — Debbie K Ware
*Assistant Examiner* — Kailash C Srivastava
(74) *Attorney, Agent, or Firm* — Dority & Manning, P.A.

(57) ABSTRACT

There is provided a method of producing a stabilized microcrystalline cellulose powder containing catalase enzyme. In the method, cellulose is thoroughly mixed with phosphate borate and catalase, rinsed with water and a surfactant added. The stabilized powder may be mixed with various skin solutions (lotions, ointments and the like). The catalase enzyme can catalyze the reaction of peroxide to oxygen.

7 Claims, No Drawings

PREPARATION OF STABILIZED CATALASE ENZYMES WITH A SURFACTANT

This application claims priority to U.S. Provisional Application Ser. No. 61/769,407, filed on Feb. 26, 2013, which is incorporated herein in its entirety by reference thereto.

BACKGROUND

The present disclosure relates to a method of stabilizing catalase enzymes for longer term storage and stability until use. This disclosure also relates to the stabilized enzymes.

Oxygen is essential to sustaining life. Marine life utilize oxygen in dissolved form whereas land based species including humans utilize gaseous oxygen. The lack of oxygen or hypoxia is commonly experienced by people in their extremities (e.g. feet) as they get older due to poor blood circulation as well as by those with conditions such as diabetes. Studies have also shown below normal, low oxygen tension in the skins of older people. This often leads to poor skin health and an excessive presence of visible conditions such as wrinkles, dryness and lower skin elasticity. Over the years, cosmetic manufacturers have introduced skin formulations with a large variety of ingredients such as emollients, exfoliators, moisturizers etc., to retard these age related effects and improve and maintain skin health. Few formulations have focused on the direct delivery of oxygen to the skin.

Oxygen delivery to the skin has been examined for medical use, e.g. in treating of the compromised skin (wounds, inflammation and trauma) and more recently, intact skin. For example, Ladizinsky patented an oxygen generating wound dressing (U.S. Pat. No. 5,792,090). More recently, Gibbins et al. patented a method of making an oxygen generating foam dressing based on a polyacrylate polymer (U.S. Pat. No. 7,160,553). While the method of making an oxygen generating foam dressing is straightforward, the dressing itself suffers from a few drawbacks. For instance, the shelf life of the dressing is insufficient because oxygen from the dressing diffuses out of the foam cells over time. An alternative to the foam dressing in the form of an on-demand oxygen generating topical composition was proposed to overcome the limitation of the short shelf life (Ladizinsky US2009/0074880). In the '880 publication, a gel containing a catalyst and a peroxide in a separate reservoir, are brought together immediately before applying the mixture to the skin and covering it to maintain contact with the skin. Whether used for cosmetic applications or medical applications, oxygen generation is generally achieved though the catalytic decomposition of a peroxide, commonly hydrogen peroxide.

In any of the applications using catalyst and peroxide, a problem that has been found is that the catalyst can become inactivated during storage in a short period of time. Elevated temperatures accelerate this inactivation for many catalysts. For modern shipping and customer usage, it is important that the product be stable for a period of time sufficient to package, ship, market and sell it and to be stable in the user's home or other location. The stabilization of peroxide and/or a catalyst in a composition would be a step forward that would allow long term storage of the product. It would also be desirable if the product were stable at elevated temperatures commonly found in the shipping industry.

There is a need for a way of stabilizing a catalyst and/or peroxide for extended periods of time and at elevated temperatures. This would allow for the production, packaging, storage and shipping of a product without the product becoming deactivated before the customer was able to use it.

SUMMARY

There is provided a way of stabilizing a catalyst, particularly catalase, so that it may remain stable for an extended period of time. There is also provided a way of stabilizing a catalyst at elevated temperatures.

In the method, a substrate such as cellulose is thoroughly mixed with phosphate borate and catalase, rinsed with water and a surfactant added. The stabilized powder may be mixed with various skin solutions (lotions, ointments and the like). The catalase enzyme can catalyze the reaction of peroxide to oxygen.

DETAILED DESCRIPTION

Described below are methods of stabilizing catalase so that it may be stored without becoming deactivated. Catalase, an enzyme commonly produced by bacteria and fungi, can be used as a catalyst to decompose peroxide to oxygen. This decomposition is extremely rapid, but does depend on having a sufficient amount of catalase for a given amount of peroxide in order to be successful. Catalase can easily become inactivated over time so stabilizing the catalase can extent its useful lifetime and improve its commercial viability. Stabilization at higher temperatures is also important since temperatures experienced during shipping can be high enough to inactivate many catalysts.

Note that although the examples use microcrystalline cellulose as the substrate, any suitable substrate may be used, including ceramics and metals.

The following procedure is a commonly accepted method of measuring catalase activity that is used to determine how well the catalase maintains its activity after stabilization and storage. After that are examples of the preparation of the disclosed stabilized catalase.

Analyzing for Catalase Activity

The activity of catalase enzyme is defined in International Units (IU). A solution or solid powder (in suspension) is defined to have an activity of one IU/ml or g if it can decompose 1 micromole of hydrogen peroxide per ml per minute at 25 C and pH 7. During the analysis for catalase activity, the hydrogen peroxide concentration is preferably maintained between 10 and 50 mM.

The analytical procedure for measuring catalase activity is straightforward and is known to those of ordinary skill in the enzyme industry. Briefly, following the addition of catalase solution of unknown concentration to the hydrogen peroxide solution, the peroxide absorbance value at 240 nm is monitored over time using a UV visible spectrophotometer. Since the optical density is linearly related to peroxide concentration, using the absorbance versus time data, the concentration of peroxide versus time data is obtained. Note that the molar extinction coefficient of hydrogen peroxide at 240 nm is 39.4 liter/mol-cm. From the kinetic data, the initial rate (at time 0) is obtained and used to calculate the catalase activity.

EXAMPLE 1

Preparation of Cellulose Adsorbed Catalase-Tween 20 Slurry (CCT-A) (0188-45/48)

The objective was to examine if the catalase activity is retained to a greater extent in a wet form (slurry).

In an empty pre-weighed conical bottom PP tube (BD Falcon), a weighed quantity (0.5 g) of microcrystalline powder (Avicel® PC105) was added. This addition was followed by 4.5 ml phosphate borate buffer (0.05M, pH: 6.7) and a sufficient amount of catalase enzyme solution (Grade 1500L, Activity: 50,000 IU/ml from BIO-CAT Inc. of Troy, Va.) was added for a target theoretical activity of CCT-A of ~10,000 IU/g. The contents were briefly mixed on a vortex mixer and the tube was placed on a shaker set at 800 rpm for 24 h.

After 24 h, the liquid from the tube was drained and the remaining solids were rinsed three times with 5 ml de-ionized water. After each rinse, the solids were centrifuged and the supernatant liquid was discarded. The wet cellulose solids adsorbed with catalase was weighed and measured ~1.33 g, implying roughly 0.83 g of moisture was present. Next, the activity of catalase adsorbed on cellulose was measured and found to be 2396 IU/g. To the wet cellulose in the conical PP tube, 2.67 g Tween 20 surfactant was added and the contents vortexed to uniformity to yield dull green colored viscous slurry of CCT-A (~4.0 g).

EXAMPLE 2

Effect of Thermal Cycling on the Activity of CCT-A (0188-45/48 & 0190-30/31)

Any commercial preparation of catalase must be able to withstand, without loss of substantial activity, thermal stresses generated in the course of shipping under different environmental conditions. We tested the CCT-A sample prepared in Example 1 under a full thermal cycle consisting of three stages. The first stage maintained the sample at −20 C for 72 h; second stage at 40 C for 72 h and third and final stage at 55C for 6 h. Thereafter the sample was cooled to room temperature and tested for activity. The results were as follows:

| Condition | Activity (IU/g) |
|---|---|
| Before cycling | 2396 |
| After cycling | 2695 |

Though the activity value after cycling measured greater than starting value, it should be not construed that thermal cycling improved activity, but rather that a loss of activity did not occur. The reason for higher activity might lay in the way the activity was calculated. In the present method for calculating activity, its value is very sensitive to the initial rate value obtained from the kinetic data.

With any sample that has been subjected to thermal cycling, the property under measurement may not display degradation immediately but may do so after some time after the completion of the cycling test. We wanted to examine if this was the case. The catalase slurry sample after thermal cycling was maintained at room temperature for 7 weeks and its activity measured at time intervals. The results are listed below.

| Duration | Activity (IU/g) |
|---|---|
| 1 week after cycling | 2856 |
| 5 weeks after | 2592 |
| 7 weeks after | 2455 |

The activity values observed after 1, 5 and 7 weeks respectively are comparable to the initial value seen for the CCT-A sample. Clearly the stabilization of activity is seen over 7 weeks after thermal cycling indicating that the method of preparing CCT-A affords us a robust formulation.

EXAMPLE 3

Increasing the Starting Activity of CCT-A Formulation and Scale Up Experiments

In Example 1, the initial catalase activity of the CCT-A formulation was on the order of 2500 IU/g. This value was considered low partly due to lower transfer efficiency of catalase from the liquid to the adsorbed state. We investigated whether using high potency catalase powder along with catalase liquid formulation would yield a robust, high catalase concentration formulation without the need of adsorption, that then could be blended into base cosmetic lotions, ointments or creams at very low levels so as not to alter their physical characteristics.

TABLE 1

| Blends of catalase Tween 20 slurry made (5 g scale) | | | |
|---|---|---|---|
| Ingredient | 0193-04F1 | 0193-04F2 | 0193-04F3 |
| Catalase 1500L* | 2.000 g | 1.500 g | 1.875 g |
| Catalase 7500* | 0.375 g | 0.750 g | 0.625 g |
| Avicel PC105 | 1.250 g | 0.750 g | 0.750 g |
| Tween 20 | 1.375 g | 2.000 g | 1.750 g |
| Total | 5.000 g | 5.000 g | 5.000 g |
| Target theoretical activity | 40,000 IU/g | 50,000 IU/g | 50,000 IU/g |
| Actual measured activity | 33,060 IU/g | 52,080 IU/g | 45,600 IU/g |

*Catalase 1500L & Catalase 7500 is liquid and solid catalase formulations with 50,000 and 250,000 IU/g activity respectively, from BIO-CAT Inc.

In preparing any of the above compositions, Catalase 7500 was dissolved in Catalase 1500 L. To the catalase solution, weighed quantities of cellulose powder and Tween 20 were added and the contents mixed to uniformity. Three blends of catalase Tween 20 slurry were made in the varying compositions with target activities of either 40,000 IU/g or 50,000 IU/g. When measured, the actual activity values were slightly off in two compositions. Nonetheless, they were comparable to the target values suggesting we could produce whatever value we chose simply by manipulating the quantities of commercial catalase preparations. Note that none of the 3 formulations (referred to as COTS) listed in the Table 1 required an adsorption step.

As to the ease of blending into either lotion or cream, Formula 04F1 and 04F2 were not optimal. Formula 04F1 was hard to blend into a Skin hydrator lotion and Formula 04F2 made the lotion somewhat watery. Formula 04F3 was observed to blend in the best, yielding a smooth and fluid lotion. In the test blends with lotion, no more than 10% of the above formulae were used.

Scale Up Experiments

In order to demonstrate we could blend any of the above COTS formulae to a target activity value even on a large scale, we prepared three 100 g batches of COTS Formula 0193-04F3 with catalase activity target of 50,000 IU/g. Using any 100 g batch, one could nearly make ~5 kg of a lotion having catalase activity of 1000 IU/g justifying that 100 g scale was a good representation of successful scale up.

TABLE 2

Activity Measurements of CCTS Made on 100 g Scale

| Parameter | 0190-62B1 | 0190-62B2 | 0190-62B3 |
|---|---|---|---|
| Target activity value | 50,000 IU/g | 50,000 IU/g | 50,000 IU/g |
| Meas. Activity value | 50,580 IU/g | 53,660 IU/g | 51,700 IU/g |
| Meas. Activity value after 8 weeks @ 4 C. | 46,320 IU/g | 50,800 IU/g | Not measured |

There were no problems in the preparation of 100 g scale COTS batches. Using tabletop mixers, the blends were readily prepared in glass beakers and the procedure could be readily scaled up appropriately. The proximity of the actual measured activity values to the target value confirmed that the prepared blends were uniform compositions. When not used, the sample batches were stored at 4 C. Interestingly, their activities remained practically unchanged (average decrease of ~6%) under this storage condition. Considering that catalase is protein matter and susceptible to bacteria or fungi induced degradation, the present results are surprising.

EXAMPLE 4

Thermal Aging Study of Emulsion Composition Blended With CCTS Formula

The aim of this study was to thermally age the emulsion composition with COTS at 40 C for 12 weeks following a thermal shock of 55 C for 6 h. The thermal shock was to simulate elevated temperature conditions during shipping (we omitted the prolonged 40 C and −20 C exposures because we found 55 C exposure produced the greatest impact). The accelerated aging as simulated by 40 C exposure for 12 weeks translated into 2 years real-time shelf life under cosmetic industry accepted norms if the specified performance criterion was met.

COTS Formula 0193-04F3 sample from Example 3 was blended into the base Skin Hydrator lotion formula 1553-07 supplied by BenchMark Laboratories of Fountain Valley, Calif. to obtain two lotion samples, each with 1000 IU/g and 500 IU/g. The samples were (i) subjected to 55 C for 6 h and then (ii) placed in an oven at 40 C.

Each week, the samples were removed, cooled to room temperature and tested for efficacy. To test for efficacy, each sample aliquot (~0.5 g) was mixed in 1:1 proportion with identical quantity of 0.9% hydrogen peroxide containing lotion (O2 Reservoir from BenchMark Laboratories, Formula 1574-06). The 1:1 mix after 20 minutes was analyzed for residual peroxide by HRP assay. As control, O2 Reservoir (maintained at room temperature) was analyzed for peroxide. From the value of peroxide in O2 Reservoir and the residual peroxide value, the percent decomposition of hydrogen peroxide was determined.

The performance criterion for the catalase-containing lotion samples was the demonstration of at least 60% decomposition of hydrogen peroxide in 1:1 mix after 20 minutes elapsed time. Ideally, if there was no loss of catalase activity, the percent peroxide decomposition would be 100%.

The accelerated age test results are presented in Table 3. The data below reveal that catalase containing lotion with 1000 IU/g starting activity is able to retain ability to decompose peroxide practically completely though the 500 IU/g barely falls short of the specified criterion of 60% minimum peroxide decomposition.

In contrast the results of two SH samples with the same levels of activity but prepared by blending in the catalase liquid (BIOCAT Inc. Grade 1500L) directly without Tween 20 and microcrystalline cellulose are quite different (see bottom two rows, Table 3). Both samples lost catalase activity when exposed to 55 C for 6 h by 26% and 59% when compared to samples made using Tween 20 stabilization method. When these two samples were aged at 40 C for over 12 weeks, they lost catalase activity by an average of ~10% on top of the earlier loss.

When the efficacy results were compared at the conclusion of age testing (12 weeks at 40 C), the stabilization effect due to Tween 20 and cellulose was apparent. The stabilization slowed down the catalase activity loss by a factor of 1.5. To wit, the 1000 IU samples with and without Tween 20 registered $H_2O_2$ decomposition rates of 95% and 64% respectively while the corresponding 500 IU samples exhibited decomposition rates of 57% and 32% respectively.

While to some a factor of 1.5 may not seem much. However, it means one needs only 2/3 as much catalase, an expensive biochemical to achieve comparable decomposition efficacies when employing Tween 20/Cellulose stabilization method. The two chemicals used in stabilizing catalase are commodity chemicals and relatively inexpensive. Thus, the stabilization method of the present invention offers clear advantages over the prior art.

TABLE 3

Accelerated Age Test (@ 40 C.) Results for Skin Hydrator Lotion Samples with CCTS Formula 0193-04F3 After Thermal shock @55 C./6 h

| Sample ID | Start | Wk 1 | Wk 2 | Wk 3 | Wk 4 | Wk 5 | Wk 6 | Wk 7 | Wk 8 | Wk 9 | Wk 10 | Wk 11 | Wk 12 |
|---|---|---|---|---|---|---|---|---|---|---|---|---|---|
| 0193-08/1000 IU | 100% | 99% | 99% | 93% | 95% | ND | ND | 90% | ND | 95% | ND | 95% | 95% |
| 0193-08/500 IU | 100% | 69% | 66% | 64% | 67% | ND | ND | 57% | ND | 52% | ND | 56% | 57% |
| 0195-06B/1000 IU | 74% | 59% | ND | 62% | ND | 65% | ND | ND | ND | 61% | ND | ND | 64% |
| 0195-06C/500 IU | 41% | 33% | ND | 38% | ND | 37% | ND | ND | ND | 37% | ND | ND | 32% |

As illustrated by the Examples, there is herein provided a method of preparing stabilized microcrystalline cellulose through the steps of thoroughly mixing microcrystalline cellulose powder, phosphate borate and catalase enzyme to create a mixture having solids and liquid. The liquid is then drained from the mixture and the remaining solids are rinsed with water and a surfactant is added, and the mixture is dried.

In addition to the stabilization of catalase as described herein, it has also been unexpectedly found that among the catalase derived from different organisms, the one derived from a fungus, *Aspergillus niger*, was most stable to thermal and chemical environments encountered. The catalase in buffered solution, in the adsorbed state on cellulose resisted degradation by heat or chemicals ingredients in cosmetic compositions and retained the necessary activity to produce compositions that survived rigorous shipping protocols and prolonged ageing under heat to simulate accelerated ageing.

Those ordinarily skilled in the art will recognize numerous strains of fungus are commercially available, though a desirable catalase source is fungus *Aspergillus niger*. It is important to note that this disclosure encompasses catalase derived from any source, including any fungal strain. The catalase molecules derived from *A. niger*, however, have been known to contain manganese atoms. Catalase may also be derived from genetically modified organisms where the catalase producing vector may be derived from *A. niger* or fungus in general and the host organisms in which the vector is inserted may be a fungus or another organism. Thus, in a broader aspect, the present disclosure encompasses catalase having manganese atom or atoms within its molecular structure regardless of which fungal or other organisms it is derived from. Catalase with manganese atoms in its molecular structure and having molecular weights <500,000 daltons are desirable.

The invention claimed is:

1. A method of preparing stabilized catalase enzyme comprising the steps of mixing a substrate comprising microcrystalline cellulose powder, a buffer, and catalase enzyme having a molecular weight of less than 500,000 Daltons to create a mixture including solids and liquid, draining the liquid from the mixture, rinsing the solids with water, and then adding a surfactant to the washed solids, wherein the stabilized catalase enzyme exhibits a decreased loss in catalase activity compared to catalase enzyme not mixed with the substrate and the surfactant, wherein the stabilized catalase enzyme has an activity at 25° C. between 500 IU/g and 1,000,000 IU/g, and wherein the stabilized catalase enzyme is stable for up to 12 weeks at 35° C. after thermal cycling of the stabilized catalase enzyme at 40° C. for 72 hours and 55° C. for 6 hours.

2. The method of claim 1, wherein said catalase enzyme includes manganese atoms.

3. The method of claim 1, wherein said catalase enzyme is obtained from fungus.

4. The method of claim 3, wherein the fungus is *Aspergillus niger*.

5. The method of claim 1, wherein the surfactant comprises Tween 20.

6. The method of claim 1, wherein the stabilized catalase enzyme can decompose from 60% to 95% of hydrogen peroxide after thermal cycling when the ratio of the stabilized catalase enzyme to hydrogen peroxide is 1:1.

7. The method of claim 1, wherein the buffer comprises phosphate and borate.

* * * * *